US009921407B2

(12) United States Patent
Kasai

(10) Patent No.: US 9,921,407 B2
(45) Date of Patent: Mar. 20, 2018

(54) FIBER-OPTIC SCANNER HAVING VIBRATION DAMPING MEMBER AND ILLUMINATING DEVICE AND OBSERVATION INSTRUMENT HAVING THE FIBER-OPTIC SCANNER

(71) Applicant: OLYMPUS CORPORATION, Tokyo (JP)

(72) Inventor: Yasuaki Kasai, Saitama (JP)

(73) Assignee: OLYMPUS CORPORATION, Tokyo (JP)

( * ) Notice: Subject to any disclaimer, the term of this patent is extended or adjusted under 35 U.S.C. 154(b) by 190 days.

(21) Appl. No.: 14/856,982

(22) Filed: Sep. 17, 2015

(65) Prior Publication Data

US 2016/0004072 A1 Jan. 7, 2016

Related U.S. Application Data

(63) Continuation of application No. PCT/JP2013/075589, filed on Sep. 20, 2013.

(30) Foreign Application Priority Data

Mar. 18, 2013 (JP) .................................. 2013-055170

(51) Int. Cl.
*G02B 26/10* (2006.01)
*F21V 8/00* (2006.01)
(Continued)

(52) U.S. Cl.
CPC ........ *G02B 26/103* (2013.01); *A61B 1/00172* (2013.01); *A61B 5/0062* (2013.01);
(Continued)

(58) Field of Classification Search
CPC .. G02B 26/103; G02B 26/101; G02B 6/0008; G02B 2006/0098; A61B 1/00172; A61B 5/0062
See application file for complete search history.

(56) References Cited

U.S. PATENT DOCUMENTS 4,832,444 A * 5/1989 Takahashi .............. A61B 18/20
385/117
2008/0004491 A1 1/2008 Karasawa
(Continued)

FOREIGN PATENT DOCUMENTS

CN 101776797 A 7/2010
JP 54067442 A * 5/1979
(Continued)

OTHER PUBLICATIONS

Extended Supplementary European Search Report dated Oct. 17, 2016 in related European Patent Application No. 13 87 8637.1.
(Continued)

*Primary Examiner* — Que T Le
*Assistant Examiner* — Jennifer Bennett
(74) *Attorney, Agent, or Firm* — Scully, Scott, Murphy & Presser, P.C.

(57) ABSTRACT

A fiber-optic scanner equipped with a light-guiding optical fiber; the fiber-optic scanner including a plurality of vibration generating units disposed circumferentially at equal intervals on an outer peripheral surface of the optical fiber located on a base end side thereof at a predetermined distance from the emission end of the optical fiber to vibrate an emission end of the optical fiber in a plurality of directions; and a vibration damping member disposed at least in a position between base end-side edges of the vibration generating units and the emission end of the optical fiber, wherein the vibration damping member has a uniform shape of a rotating body rotated around the axis line of the optical fiber.

4 Claims, 5 Drawing Sheets

(51) Int. Cl.
*A61B 5/00* (2006.01)
*A61B 1/00* (2006.01)
*G02B 6/00* (2006.01)

(52) U.S. Cl.
CPC ......... *G02B 6/0008* (2013.01); *G02B 26/101* (2013.01); *G02B 2006/0098* (2013.01)

(56) References Cited

U.S. PATENT DOCUMENTS

| | | |
|---|---|---|
| 2010/0177368 A1 | 7/2010 | Kobayashi |
| 2010/0179386 A1 | 7/2010 | Kobayashi |
| 2013/0158393 A1* | 6/2013 | Papac ................ A61N 5/062 600/427 |

FOREIGN PATENT DOCUMENTS

| | | |
|---|---|---|
| JP | 2010-162090 A | 7/2010 |
| JP | 2011-115252 A | 6/2011 |
| JP | 2011-156235 A | 8/2011 |
| JP | 2011-217835 A | 11/2011 |
| WO | 2007/106075 A2 | 9/2007 |

OTHER PUBLICATIONS

International Search Report dated Dec. 24, 2013 issued in PCT/JP2013/075589.

* cited by examiner

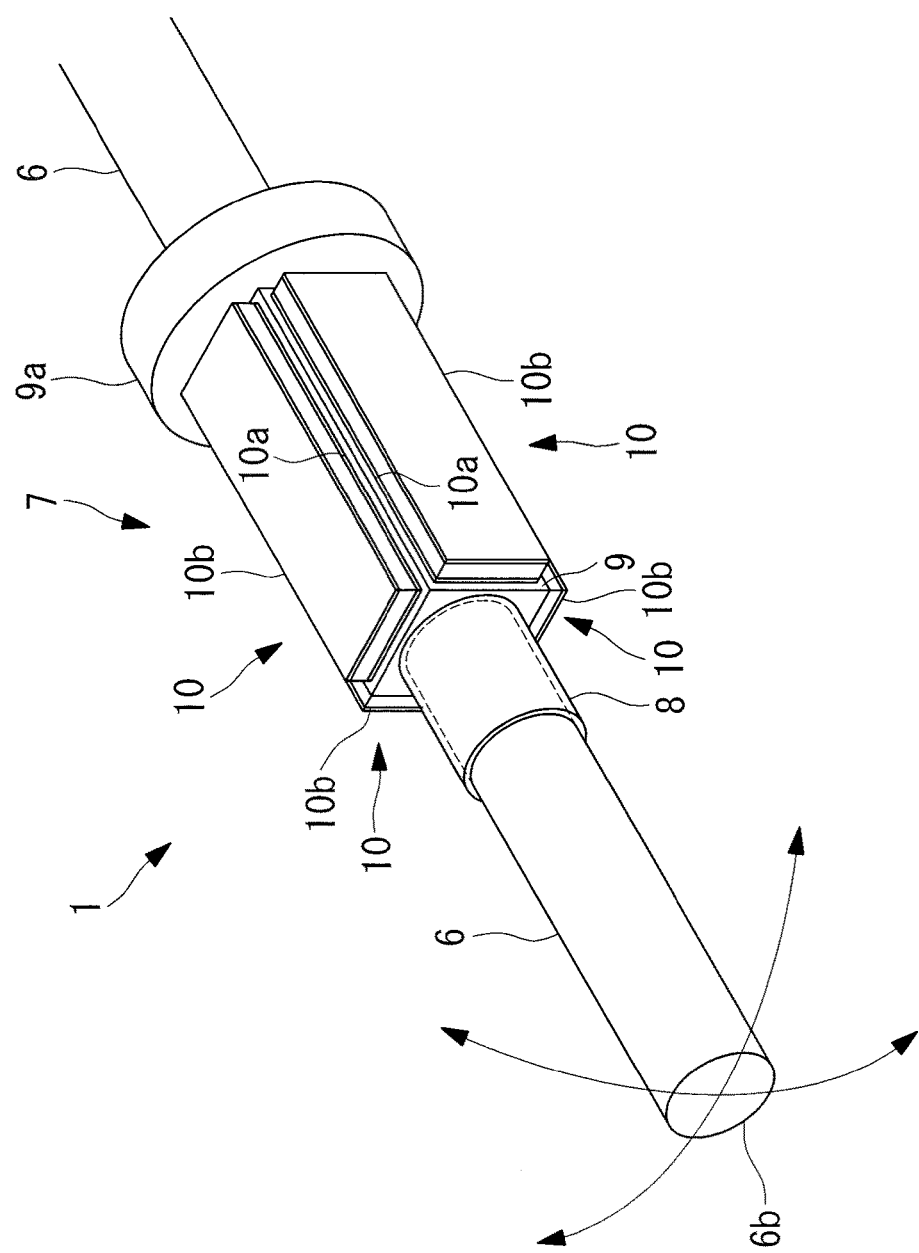

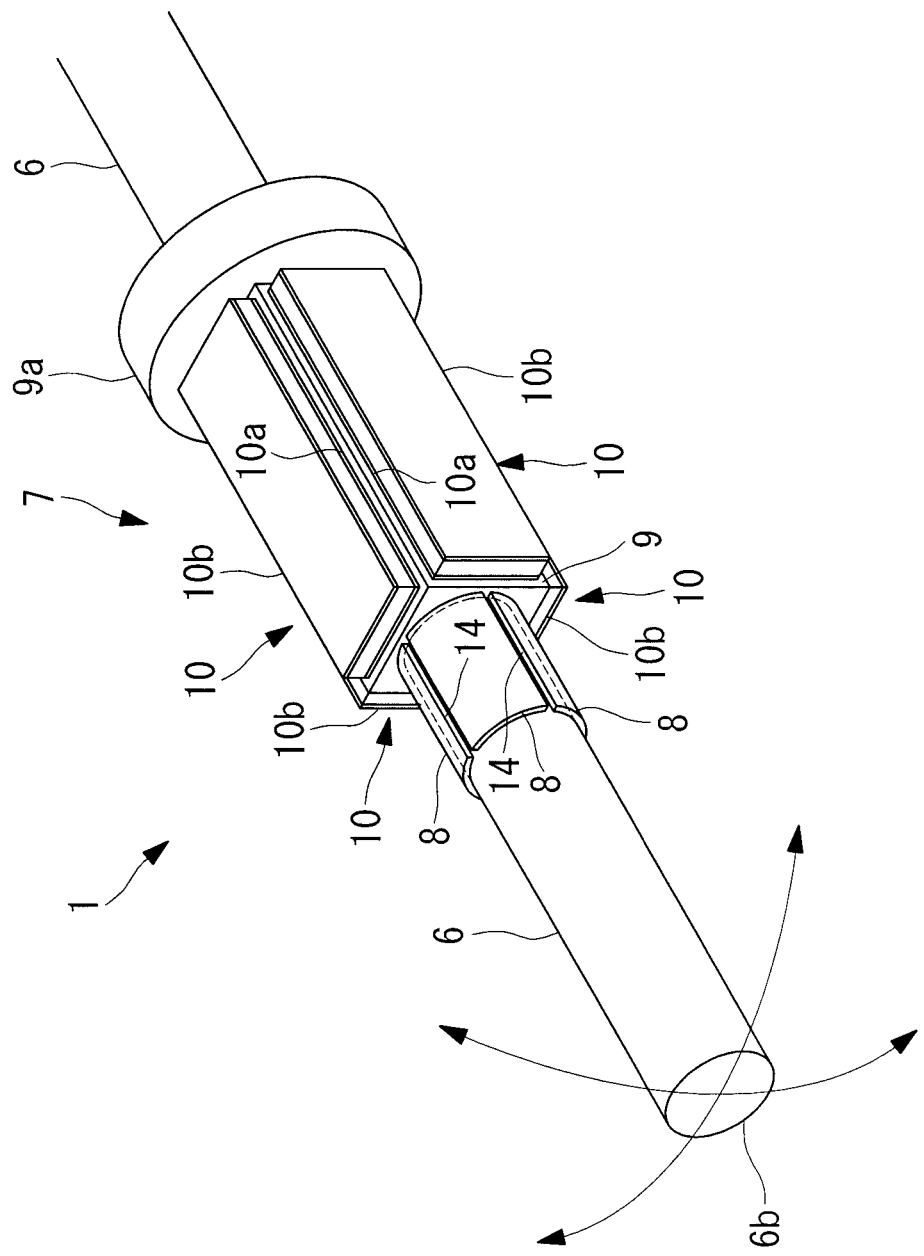

FIBER-OPTIC SCANNER HAVING VIBRATION DAMPING MEMBER AND ILLUMINATING DEVICE AND OBSERVATION INSTRUMENT HAVING THE FIBER-OPTIC SCANNER

CROSS-REFERENCE TO RELATED APPLICATIONS

This application is a Continuation Application of International Application PCT/JP2013/075589 filed on Sep. 12, 2013, which claims priority to Japanese Application No. 2013-055170 filed on Mar. 18, 2013.
The Contents of International Application PCT/JP2013/075589 and Japanese application No. 2013-055170 are hereby incorporated by reference herein in its entirety.

TECHNICAL FIELD

The present invention relates to a fiber-optic scanner, an illuminating device, and an observation instrument.

BACKGROUND ART

Conventionally, there has been known a fiber-optic scanner for scanning emitted light by vibrating the emission end of an optical fiber (see, for example, PTL 1).
This fiber-optic scanner is equipped with a column-shaped piezoelectric device (PZT tube) the emission end of which is made to penetrate through the optical fiber to protrude from one end of the optical fiber, and an electrode disposed on a surface of the piezoelectric device. The base of the optical fiber protruding from the piezoelectric device is fixed to an edge of the piezoelectric device with an adhesive agent. In this fiber-optic scanner, the flexural vibration of the piezoelectric device is transferred to the optical fiber through the adhesive agent.

CITATION LIST

Patent Literature

{PTL 1}: Japanese Unexamined Patent Application, Publication No. 2011-217835

SUMMARY OF INVENTION

Technical Problem

Since the adhesive agent is an elastic body, however, the flexural vibration of the piezoelectric device is attenuated before being transferred to the optical fiber. If the shape of the adhesive agent is non-uniform in this case, the degree of attenuation of vibration to be transferred to the optical fiber varies depending on the direction of vibration. It is therefore difficult to vibrate the leading end of the optical fiber, so as to draw, for example, a smooth helicoidally-shaped trajectory.
The present invention has been accomplished in view of the above-described circumstances. Accordingly, it is an object of the present invention to provide a fiber-optic scanner, an illuminating device and an observation instrument which enable the uniform vibration of an optical fiber and make available a desired scan trajectory.

Solution to Problem

In order to achieve the above-described object, the present invention provides the following solutions.

One aspect of the present invention provides a fiber-optic scanner equipped with a light-guiding optical fiber; a plurality of vibration generating units disposed circumferentially at equal intervals on an outer peripheral surface of the optical fiber located on a base end side thereof at a predetermined distance from an emission end of the optical fiber to vibrate the emission end of the optical fiber in a plurality of directions; and a vibration damping member disposed at least in a position between base end-side edges of the vibration generating units and the emission end of the optical fiber, wherein the vibration damping member has a uniform shape of a rotating body rotated around the axis line of the optical fiber.
According to this aspect, it is possible to scan light guided through the optical fiber and emitted from the emission end over an object along a two-dimensional trajectory by actuating the vibration generating units and vibrating the emission end of the optical fiber. In this case, the phase of part of vibrational energy varies when vibration generated at the vibration generating units propagates to the optical fiber and reflects on the edge face and the like thereof, thus derivatively generating vibration in various directions.
According to this aspect, vibration is attenuated by the vibration damping member disposed between the vibration generating units and the emission end. Thus, it is possible to leave over only the vibration in the direction of vibration excitation by the vibration generating units. In addition, vibration of various phases derivatively generated at the optical fiber is uniformly attenuated in this case by the vibration damping member formed of a uniform shape of a rotating body rotated around the axis line of the optical fiber. Thus, it is possible to prevent a variation in the phase of vibration within the optical fiber and stably scan light in a desired scanning mode.

BRIEF DESCRIPTION OF DRAWINGS

FIG. 5 is a perspective view illustrating another modified example of the fiber-optic scanner of FIG. 1.
FIG. 6 is a perspective view illustrating yet another modified example of the fiber-optic scanner of FIG. 1.

DESCRIPTION OF EMBODIMENTS

Figure 1:
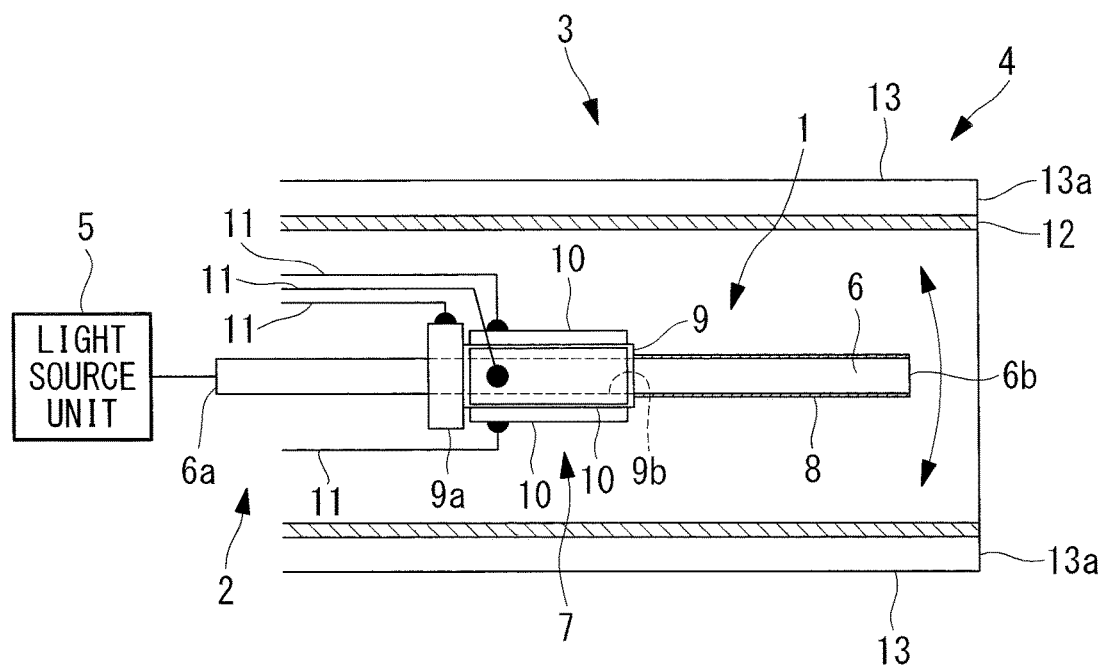
FIG. 1 is a partially cutaway side view illustrating a fiber-optic scanner, an illuminating device and an observation instrument according to one embodiment of the present invention.

A fiber-optic scanner 1, an illuminating device 2 and an observation instrument 3 according to one embodiment of the present invention will be described hereinafter with reference to the accompanying drawings.
As illustrated in FIG. 1, the observation instrument 3 according to the present embodiment is equipped with the illuminating device 2 and an observation optical system 4.
The illuminating device 2 is equipped with a light source unit 5 for emitting illuminating light; and the fiber-optic scanner 1 according to the present embodiment for guiding and scanning the illuminating light generated at the light source unit 5.

Figure 2:
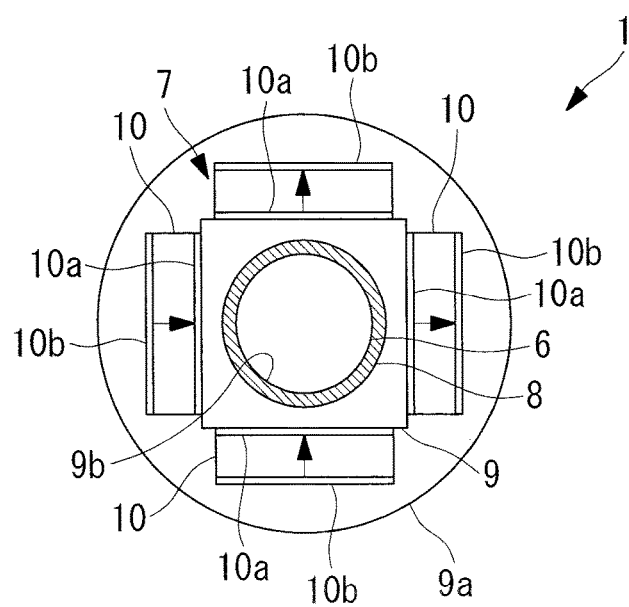
FIG. 2 is a front view illustrating the fiber-optic scanner of FIG. 1.
Figure 3:
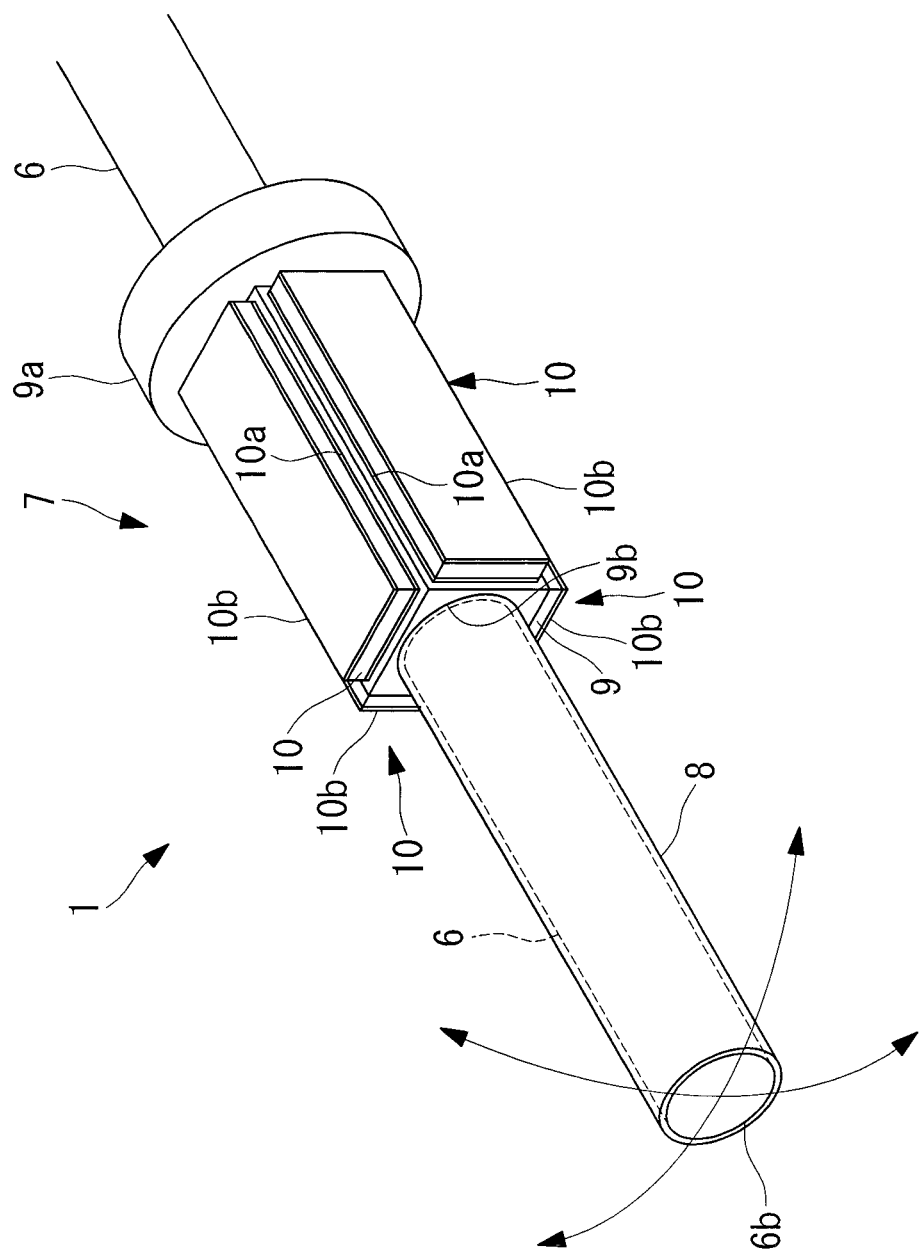
FIG. 3 is a perspective view illustrating the fiber-optic scanner of FIG. 1.

As illustrated in FIGS. 1 to 3, the fiber-optic scanner 1 is equipped with an optical fiber 6 for letting the illuminating light from the light source unit 5 enter the optical fiber 6 from the base end-side incident end 6a of the optical fiber 6, guiding the illuminating light in the longitudinal direction of the optical fiber 6, and emitting the illuminating light out of the leading end-side emission end 6b of the optical fiber 6; a vibration generating unit 7 for vibrating the emission end 6b of the optical fiber 6 in a direction orthogonal to the longitudinal axis of the optical fiber 6; and a vibration damping member 8 for attenuating generated vibration.

The vibration generating unit 7 includes a resilient portion 9 made from an electrically conductive metal material, and piezoelectric devices 10 fixed to the resilient portion 9. The resilient portion 9 has a shape in which a through-hole 9b capable of penetrating through the optical fiber 6 is formed along the longitudinal axis of a square prism including a circular flanged portion 9a at one end thereof.

Each piezoelectric device 10 is formed into a platy shape on the two through-thickness end faces of which electrodes 10a and 10b are disposed. The piezoelectric devices 10 are fixed to the square prism with the electrodes 10a placed in electrical contact with the respective side surfaces of the square prism of the resilient portion 9. Piezoelectric devices 10 disposed in positions opposed to each other across the optical fiber 6 are arranged so that the polarization directions of those piezoelectric devices are toward the same direction, as shown by arrows in FIG. 2.

A lead wire 11 used to supply a voltage signal for driving each piezoelectric device 10 is connected to each electrode 10b of the piezoelectric device 10. Lead wires 11 for supplying an in-phase voltage signal are connected to piezoelectric devices 10 disposed in positions opposed to each other across the optical fiber 6.

The vibration damping member 8 is a cylindrical member for covering the entire outer circumferential surface of a portion of the optical fiber 6 protruding from the resilient portion 9 and is composed of a resin material having flexibility. As illustrated in FIG. 2, the vibration damping member 8 has a uniform ring-like cross-sectional shape. Specifically, the vibration damping member 8 is shaped to have the same mechanical characteristics in all circumferential directions of the optical fiber 6, i.e., has the shape of a rotating body rotated around the longitudinal axis of the optical fiber 6.

As illustrated in FIG. 1, the observation optical system 4 is equipped with a plurality of optical fibers 13 for detection laid out on the outer periphery of a tubular observation instrument main unit 12 for housing the fiber-optic scanner 1 in the circumferential direction of the observation instrument main unit 12. The optical fiber 13 is fixed with the incident end 13a thereof facing toward the emission end 6b side of the optical fiber 6. Accordingly, return light, such as reflected light and fluorescent light, returning to the observation instrument 3 side as the result of illuminating light emitted from the emission end 6b of the optical fiber 6 of the fiber-optic scanner 1 being radiated to an object is received at the incident ends 13a of the plurality of optical fibers 13 and detected by an unillustrated optical detector disposed on the base end side of the observation instrument main unit 12.

Hereinafter, a description will be made of the operation of the fiber-optic scanner 1, the illuminating device 2 and the observation instrument 3 according to the present embodiment configured as described above.

In order to observe an object using the observation instrument 3 according to the present embodiment, the illuminating device 2 is actuated to radiate illuminating light to the object.

When the illuminating device 2 is actuated, illuminating light generated by the light source unit 5 is guided by the optical fiber 6 and emitted from the emission end 6b of the leading end of the optical fiber 6 toward the object. At this time, the emission end 6b can be vibrated by driving the fiber-optic scanner 1 to two-dimensionally scan the illuminating light over the object.

Return light, such as reflected light and fluorescent light, is generated at the object as the result of the illuminating light being radiated, and returns to the observation instrument 3 side. Accordingly, the return light is received at the incident ends 13a of the optical fibers 13 for detection provided in the observation instrument main unit 12. The return light propagating through the optical fibers 13a is thus detected with an optical detector on the base end side. Along with this operation, intensity information on the return light is correlated with a position at which the illuminating light is scanned by the fiber-optic scanner 1 to store the correlations. Consequently, it is possible to obtain two-dimensional images of the object.

In this case, the fiber-optic scanner 1 applies an alternating voltage to the four piezoelectric devices 10 constituting the vibration generating unit 7 to two-dimensionally vibrate the emission end 6b of the optical fiber 6. For example, piezoelectric devices 10 disposed oppositely to each other across the optical fiber 6 are paired and sinusoidal voltage signals the maximum amplitude of which varies sinusoidally are applied at constant time intervals to two pairs of piezoelectric devices 10 with the phases of the voltages differentiated by 90°. Consequently, it is possible to vorticosely vibrate the emission end 6b and vorticosely scan the illuminating light over the object.

In this case, according to the fiber-optic scanner 1 in accordance with the present embodiment, vibration is attenuated by the vibration damping member 8 provided so as to cover the optical fiber 6.

Since the vibration damping member 8 has the shape of a rotating body rotated around the longitudinal axis of the optical fiber 6, the vibration damping effect of the vibration damping member 8 is uniform over the entire circumference of the optical fiber 6. As a result, relatively small-amplitude vibration derivatively generated within the optical fiber 6 in directions other than the direction of vibration excitation by the vibration generating unit 7 is sufficiently attenuated. Thus, only the vibration in the direction of vibration excitation is propagated to the optical fiber 6. Consequently, it is possible to suppress a variation in the vibration phase of the optical fiber 6.

That is, the fiber-optic scanner 1 has the advantage of being able to vibrate the emission end 6b of the optical fiber 6, so as to draw a smooth trajectory correctly following the waveforms of driving signals supplied to the piezoelectric devices 10 through the lead wires 11. As a result, according to the fiber-optic scanner 1 and the illuminating device 2 in accordance with the present embodiment, it is possible to scan the illuminating light correctly following, for example, a desired whorl-like scan trajectory. In addition, according to the observation instrument 3 in accordance with the present embodiment, it is possible to improve the accuracy of positions, at which the illuminating light is scanned, to be correlated with the intensity of detected return light. Thus, the observation instrument 3 has the advantage of being able to form distortion-free images and improve observational accuracy.

Note that in the present embodiment, the vibration damping member 8 is formed into a cylindrical shape. Alternatively, however, the vibration damping member 8 may be formed into other optional shapes of rotating bodies. The mechanical characteristics of the vibration damping member 8 can be made uniform in all circumferential directions of the optical fiber 6 as long as the vibration damping member 8 is rotating body-shaped. Thus, it is possible to uniformly attenuate vibrational components in directions other than the direction of vibration excitation, and effectively suppress the variation of a vibration phase.

Figure 4:
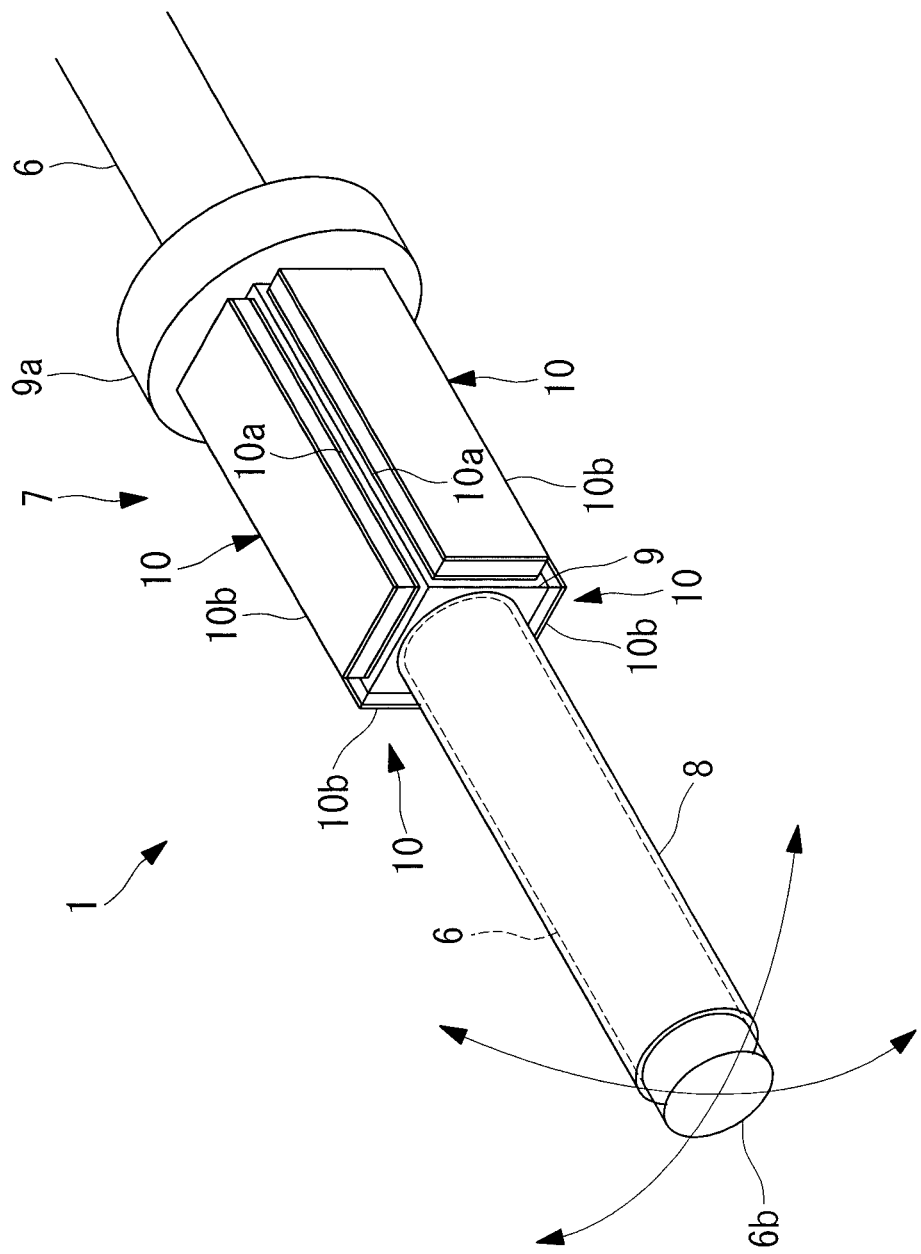
FIG. 4 is a perspective view illustrating a modified example of the fiber-optic scanner of FIG. 1.

Also note that in the present embodiment, the vibration damping member 8 is disposed so as to cover the entire side surface of a portion of the optical fiber 6 protruding from the resilient portion 9. Alternatively, however, the vibration damping member 8 may be disposed in a position to cover the side surface of the optical fiber 6, so as to partially expose only the leading end of the optical fiber 6, as illustrated in FIG. 4. Yet alternatively, the vibration damping member 8 may be disposed on only part of the portion of the optical fiber 6 protruding from the resilient portion 9 adjacent to the resilient portion 9, as illustrated in FIG. 5. Still alternatively, the vibration damping member 8 may be disposed so as to expose only the portion adjacent to the resilient portion 9.

The vibration damping member 8 may be partially disposed in a halfway position between the base end-side edges and the emission end-side edge of the vibration generating unit. Alternatively, the vibration damping member 8 may be disposed from a halfway position within the vibration generating unit to the edge of the vibration generating unit on the emission end 6b side of the optical fiber 6. Yet alternatively, the vibration damping member 8 may be disposed from a halfway position within the vibration generating unit to a halfway position between the edge of the vibration generating unit on the emission end 6b side of the optical fiber 6 and the emission end 6b. Still alternatively, the vibration damping member 8 may be disposed from a halfway position within the vibration generating unit to the emission end 6b of the optical fiber 6.

The vibration damping member 8 may be disposed from the edge of the vibration generating unit on the incident end 6a side of the optical fiber 6 to a halfway position within the vibration generating unit. Alternatively, the vibration damping member 8 may be disposed over the entire length of the optical fiber 6 from the edge of the vibration generating unit on the incident end 6a side of the optical fiber 6 to the edge on the emission end 6b. Yet alternatively, the vibration damping member 8 may be disposed from the edge of the vibration generating unit on the incident end 6a side of the optical fiber 6 to a halfway position between the edge on the emission end 6b side of the optical fiber 6 and the emission end 6b. Still alternatively, the vibration damping member 8 may be disposed from the edge of the vibration generating unit on the incident end 6a side of the optical fiber 6 to the emission end 6b of the optical fiber 6.

The vibration damping member 8 may be disposed from a halfway position between the incident end 6a of the optical fiber 6 and the edge of the vibration generating unit on the incident end 6a side of the optical fiber 6 to a halfway position within the vibration generating unit. Alternatively, the vibration damping member 8 may be disposed from a halfway position between the incident end 6a of the optical fiber 6 and the edge of the vibration generating unit on the incident end 6a side of the optical fiber 6 to the edge of the vibration generating unit on the emission end 6b side of the optical fiber 6. Yet alternatively, the vibration damping member 8 may be disposed from a halfway position between the incident end 6a of the optical fiber 6 and the edge of the vibration generating unit on the incident end 6a side of the optical fiber 6 to a halfway position between the edge of the vibration generating unit on the emission end 6b side of the optical fiber 6 and the emission end 6b. Still alternatively, the vibration damping member 8 may be disposed from a halfway position between the incident end 6a of the optical fiber 6 and the edge of the vibration generating unit on the incident end 6a side of the optical fiber 6 to the emission end 6b of the optical fiber 6.

The vibration damping member 8 may be disposed from the incident end 6a of the optical fiber 6 to a halfway position within the vibration generating unit. Alternatively, the vibration damping member 8 may be disposed from the incident end 6a of the optical fiber 6 to the edge of the vibration generating unit on the emission end 6b side of the optical fiber 6. Yet alternatively, the vibration damping member 8 may be disposed from the incident end 6a of the optical fiber 6 to a halfway position between the edge of the vibration generating unit on the emission end 6b side of the optical fiber 6 and the emission end 6b.

Also note that in the present embodiment, the vibration damping member 8 is formed into a cylindrical shape, so as to cover the entire circumference of the optical fiber 6. Alternatively, however, the vibration damping member 8 may be formed into a plurality of circular-arc platy shapes arranged by being equally divided, with gaps 14 thereamong, in the circumferential direction of the optical fiber 6, as illustrated in FIG. 6. In this case, vibration in the direction of vibration excitation by each piezoelectric device 10 is prevented from being attenuated by placing a gap 14 in a circumferential position associated with each piezoelectric device 10. Thus, it is possible to more efficiently vibrate the optical fiber 6.

In the above-described aspect, the vibration damping member may be disposed over the entire length of the optical fiber from the vibration generating units to the emission end.

With this configuration, it is possible to attenuate vibrational components other than vibration in the direction of vibration excitation by the vibration generating units to the utmost extent.

In addition, in the above-described aspect, the vibration damping member may be disposed from a position adjacent to the vibration generating units up to a position halfway through the optical fiber in the longitudinal direction thereof.

With this configuration, it is possible to reduce stress concentration at the position adjacent to the vibration generating units due to the vibration of the optical fiber and improve durability.

Yet additionally, in the above-described aspect, the vibration damping member may be circumferentially divided with gaps left therein in circumferential positions corresponding to the positions of the vibration generating units.

With this configuration, spaces among the vibration damping members allow vibration in the direction of vibration excitation by the vibration generating units to be propagated to the optical fiber without being attenuated. Thus, it is possible to efficiently vibrate the optical fiber.

Another aspect of the present invention provides an illuminating device equipped with one of the above-described fiber-optic scanners; and a light source unit for emitting light to be scanned by the fiber-optic scanner.

According to this aspect, light emitted from the light source unit can be guided by the optical fiber vibrated by the vibration generating units of the fiber-optic scanner and emitted from the emission end of the optical fiber to two-dimensionally scan the light over an object. In this case, the vibration phase of the optical fiber is prevented by the vibration damping unit from variation. Thus, it is possible to stably radiate light according to a desired trajectory.

Yet another aspect of the present invention provides an observation instrument equipped with the above-described illuminating device; and an optical detection unit for detecting return light returning from an object as the result of light being radiated to the object by the illuminating device.

According to this aspect, light is radiated by the illuminating device according to a desired trajectory. Consequently, it is possible to precisely correlate return light detected by the optical detector with a position where the return light is generated. Thus, it is possible to prevent the distortion of images and improve observational accuracy.

Advantageous Effect of Invention

The present invention has the advantageous effect of enabling the uniform vibration of an optical fiber and making available a desired scan trajectory.

REFERENCE SIGNS LIST

1 Fiber-optic scanner
2 Illuminating device
3 Observation instrument
4 Observation optical system (optical detection unit)
5 Light source unit
6 Optical fiber
6b Emission end
8 Vibration damping member
10 Piezoelectric device (vibration generating unit)
14 Gap

The invention claimed is:

1. A fiber-optic scanner comprising:
a light-guiding optical fiber;
a plurality of vibration generating units disposed circumferentially at equal intervals on an outer peripheral surface of the optical fiber located on a base end side thereof at a predetermined distance from an emission end of the optical fiber to vibrate the emission end of the optical fiber in a plurality of directions; and
a vibration damping member disposed over an entire length in a longitudinal direction of the optical fiber from the plurality of vibration generating units to the emission end of the optical fiber,
wherein the vibration damping member is formed of a resin material having flexibility, the vibration damping member is fixed to the optical fiber and the vibration damping member has a uniform shape of a rotating body rotated around an axis line of the optical fiber.

2. The fiber-optic scanner according to claim 1, wherein the vibration damping member is circumferentially divided with gaps left therein in circumferential positions corresponding to the positions of the vibration generating units.

3. An illuminating device equipped with one of fiber-optic scanners according to claim 1; and
a light source unit for emitting light to be scanned by the fiber-optic scanner.

4. An observation instrument comprising:
an illuminating device according to claim 3; and
an optical detection unit for detecting return light returning from an object as the result of light being radiated to the object by the illuminating device.

* * * * *